United States Patent [19]

Johnson

[11] Patent Number: 4,509,361
[45] Date of Patent: Apr. 9, 1985

[54] SOIL MOISTURE POTENTIAL DETERMINATION BY WEIGHT MEASUREMENT

[76] Inventor: Lonnie G. Johnson, 12503 S. 31st St., Omaha, Nebr. 68123

[21] Appl. No.: 556,276

[22] Filed: Nov. 30, 1983

[51] Int. Cl.³ ............................................. G01N 5/02
[52] U.S. Cl. ........................................ 73/73; 73/335
[58] Field of Search .................................. 73/73, 335

[56] References Cited

U.S. PATENT DOCUMENTS

| | | | |
|---|---|---|---|
| 1,765,816 | 6/1930 | Allen | 73/73 X |
| 2,060,957 | 11/1936 | Tarvin et al. | 73/73 |
| 2,073,611 | 3/1937 | Dunlap | 73/73 X |
| 3,520,476 | 7/1970 | Schmid | 73/73 X |
| 4,269,060 | 5/1981 | Kethley | 73/335 X |

Primary Examiner—Daniel M. Yasich

[57] ABSTRACT

An instrument for measuring soil moisture potential comprising a moisture absorber movably coupled to the soil being measured by means for maintaining said absorber in moisture potential equilibrium with said soil and permitting weight measurement of said absorber. The instrument includes scale means for weighing said absorber to determine moisture content thereof and provide an indication of soil moisture potential. The instrument includes adjustable controls for calibration.

12 Claims, 5 Drawing Figures

SOIL MOISTURE POTENTIAL DETERMINATION BY WEIGHT MEASUREMENT

BACKGROUND AND SUMMARY

The present invention provides an improved means for measuring soil moisture potential. Tensiometers and resistance blocks are predominantly employed for measuring soil moisture conditions and have limitations which are overcome by the present invention. Tensiometers require continuous maintenance and have a limited operating range. Resistance blocks generally give poor results under conditions of high soil moisture content. The improved device disclosed herein uses absorption to measure moisture potential. It has a wide operating range and does not require continuous maintenance.

An absorber which contains moisture absorbing material is physically coupled to the soil being measured by a flexible wick. The wick is designed to facilitate efficient water flow between the absorber and the soil to maintain the absorber in moisture potential equilibrium with the soil. Under equilibrium conditions, the amount of water in the absorber is determined from the absorber's weight to provide an indication of soil moisture potential.

A scale for weighing the absorber is included as an integral part of the instrument and provides a continuous reading of soil moisture potential. Electronic scales as well as mechanical scales can be employed to accomplish the necessary weight measurements. Employment of both types of scales are disclosed in the present patent. The scales employed for weighing the absorber include adjustments for calibrating soil moisture potential readings. The instrument can be calibrated to select a desired operating range and to select proportional ratios of change in moisture potential indication to change in weight (moisture content) of the absorber to provide indications of soil moisture potential in desired units.

DETAILED DESCRIPTION AND PREFERRED EMBODIMENT

Figure 1:
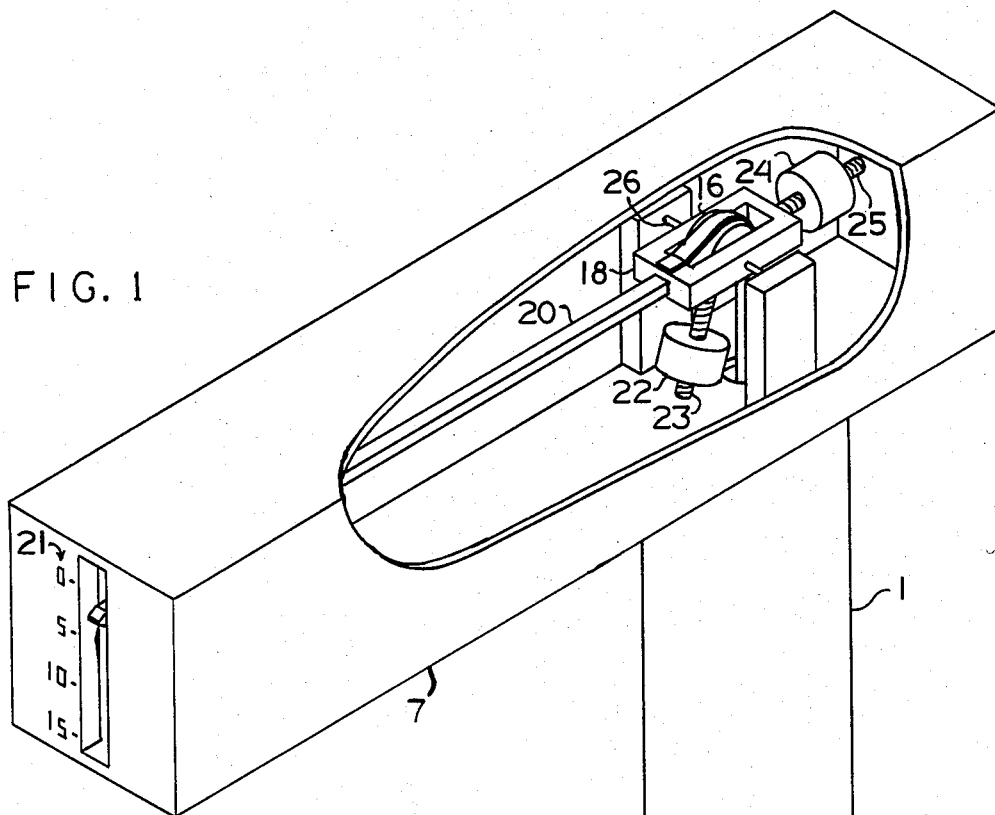
FIG. 1 shows a three-dimensional view of an embodiment of the invention. It shows cut-away views of the functional components which include the mechanical scale and the moisture absorber.
Figure 1:
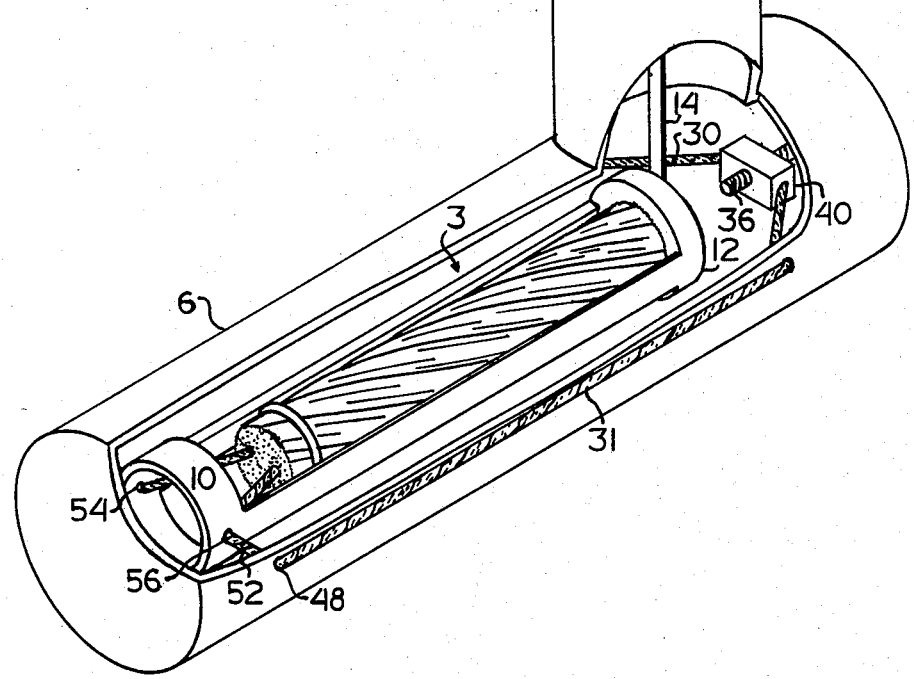
Figure 2:
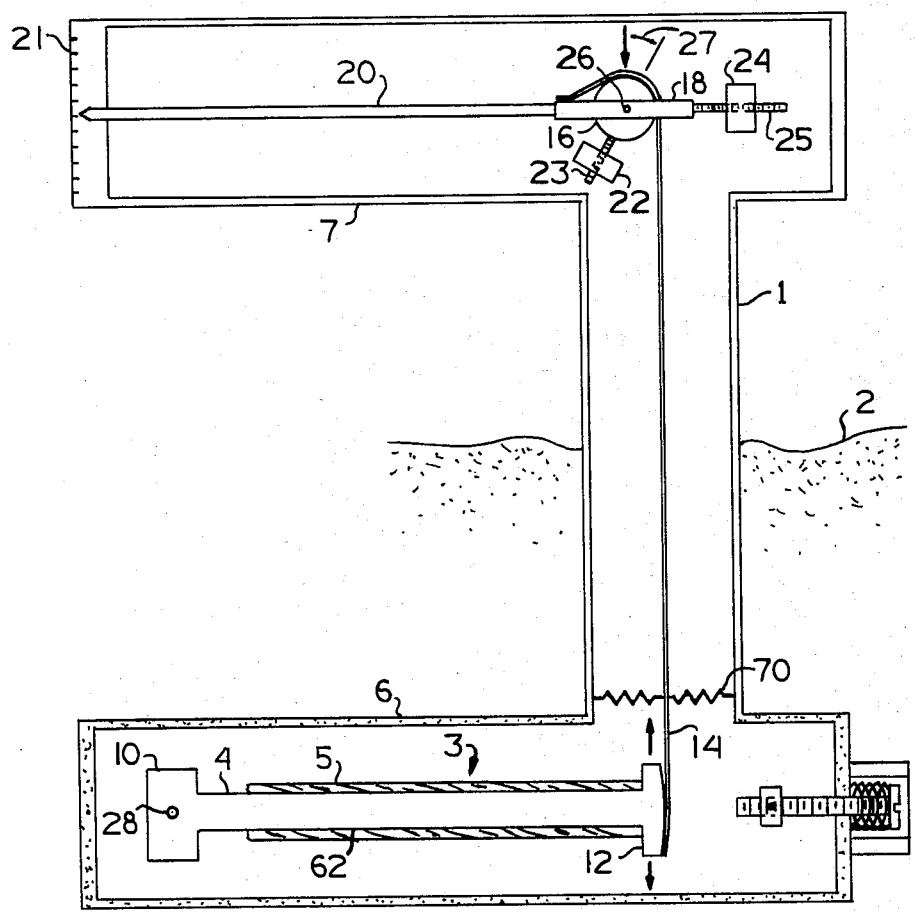
FIG. 2 is a functional diagram depicting operation of the mechanical scale to accomplish weight measurements of the absorber. The diagram also shows adjustable weights for calibrating the instruments.

An in-depth understanding of the present invention can be derived from the following description with reference to the drawings. FIG. 1 shows a three-dimensional view of an embodiment of the invention. It shows cut-away views of the elements depicted in the functional diagrams of FIGS. 2 and 3 and may be helpful when additional clarification is required. FIGS. 1 and 2 depict an all mechanical instrument. The components in the upper portion of the instrument may be replaced by those shown in FIGS. 4 and 5 to provide an electromechanical instrument as will be described later.

Referring to FIG. 2, housing structure means 1 includes subsurface chamber means 6 coupled to above ground section means 7. Structure 1 provides containment and structural mounting for the various components of the instrument. Chamber 6 is installed below ground surface 2 and in direct contact with the soil being measured for moisture potential. Absorber means 3 is comprised of mounting cradle means 4 and absorption material means 5, and is suspended inside chamber 6. Mounting cradle 4 has a bar configuration and is suspended at ends 10 and 12. Belt 14 connects end 12 to a mechanical scale means located in above ground section 7. The mechanical scale means consist of a gain calibration means comprised of a mechanical gain adjustment means which includes weight 22 and adjustment screw 23, a bias calibration means comprised of a mechanical bias adjustment means which includes weight 24 and adjustment screw 25, and an indicator means comprised of a mechanically actuated pointer means which includes pulley wheel 16, support frame 18, pointer arm 20 and graduated scale 21.

Figure 3:
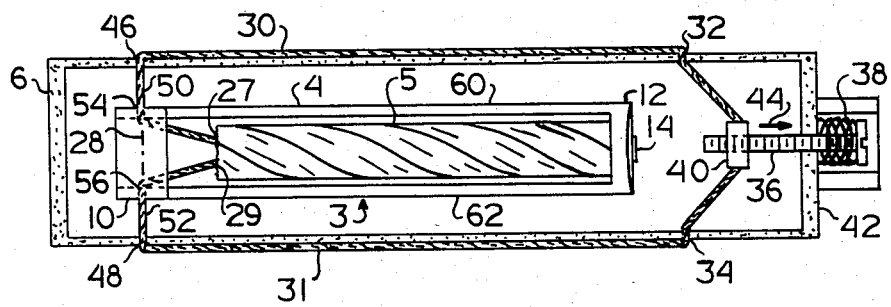
FIG. 3 shows suspension of the absorber inside the subsurface chamber by the wicks to maintain the absorber in moisture potential equilibrium with the surrounding soil and permit movement of the absorber under gravitational force for actuation of a scale.

Mounting at end 10 of cradle 4 is configured to offer minimum resistance to rotation of absorber 3 about rotation axis 28 as end 12 moves in the vertical direction. As shown in FIG. 3, rotation axis 28 is a virtual axis of rotation formed by first wick section means 50 and second wick section means 52 of flexible wick means 30 and 31, respectively. Wicks 30 and 31 extend through holes 54 and 56, respectively of end 10 and are embedded in absorption material 5 at points 27 and 29. The wicks extend through the wall of chamber 6 through holes 46 and 48 and come in direct contact with the soil being measured for moisture potential. They extend along the outside of subsurface chamber 6 and re-enter at holes 32 and 34. Internal to chamber 6, wicks 30 and 31 are attached to screw follower 40. A wick adjustment means comprised of adjustment screw 36, spring 38 and screw follower 40 is mounted to wall 42 of chamber 6 and functions to maintain wicks 30 and 31 in a high tension state. Screw 36 extends external to chamber 6 to facilitate adjustments. The wick adjust means is in effect mounted in series with wick means 30 and 31, and absorber means 3 so that the tension in wicks 30 and 31 is increased by tightening screw 36 to compress spring 38 and move follower 40 in the direction of arrow 44. Holes 32, 34, 46 and 48 in the wall of chamber 6 permit free movement of wicks 30 and 31 to allow transmission of tension along the entire lengths of the wicks. Spring 38 functions to maintain the high tension states of the wicks by expanding to compensate for creep and other material effects which could otherwise relax the wicks with age under operating conditions.

Holes 46 and 48 are on opposite sides of chamber 6. Holes 54 and 56 are on opposite sides of cradle 4 at end 10. Holes 46, 48, 54 and 56 are maintained in an in-line configuration by the high tension states of wicks 30 and 31 so that first wick section 50 and second wick section 52 form virtual axis of rotation 28 while suspending end 10 along the center line of chamber 6. Absorber 3 rotates about axis 28 through flexing of wick sections 50 and 52. The small diameters of wick sections 50 and 52 in combination with their length produce negligable restrictive torques about axis 28 for small rotation angles of absorber 3.

Absorption material 5 is attached to end 12 of cradle 4. Holes 54 and 56 are large enough to permit free movement of wicks 30 and 31 so that the tensil load applied by screw 36 is coupled through to absorption material 5. The geometry is such that the tension of wicks 30 and 31 cause side struts 60 and 62 of cradle 4 to experience a compressive load applied at end 12 by absorption material 5 and at holes 54 and 56 of end 10 by wicks 30 and 31 so that absorption material 5 is under tension.

Wicks 30 and 31 are comprised of a first very fine continuous fiber means in which multiple fibers are configured in bundles wherein each fiber extends the entire length of the wicks from screw follower 40 to attachment points 27 and 29. Absorption material 5 is comprised of a second very fine continuous fiber means in which multiple fibers are configured in bundles wherein each fiber extends the entire length of absorber 5 from attachment points 27 and 29 to end 12. The fiber means are comprised of extremely small diameter nylon fibers.

The fibers within the bundles are twisted on each other and the bundles in turn twisted in opposing directions to insure good fiber to fiber contact when under the high tension state described. This insures efficient transmission of soil moisture potential from the soil in contact with the wicks on the exterior of chamber 6 through the wicks and into absorption material 5 with good capillary action to facilitate water flow back and forth between absorption material 5 and the surrounding soil to maintain absorber 3 in moisture potential equilibrium with the soil. The amount of water within absorption material 5 and therefore, the weight of absorber means 3 provides a direct indication of the moisture potential of the surrounding soil.

Referring to FIG. 2, the weight of absorber 3 actuates the mechanical scale to provide a continuous indication of soil moisture potential. End 12 of cradle 4 is coupled by belt 14 to frame 18. Belt 14 is mounted around pulley wheel 16 so that support of absorber 3 at end 12 produces a clockwise torque about axis 26. This is in addition to the clockwise torque produced by adjustable weight 24. The torque is counterbalanced by pointer arm 20 and adjustable weight 22. As illustrated in FIG. 1, pointer arm 20 indicates the level of soil moisture potential by its position along scale 21. For low soil moisture potentials, the water content of the absorber is high causing the weight of the absorber to increase the torque about axis 26 and achieve an equilibrium condition in which pointer arm 20 is positioned toward zero. Increases in soil moisture potential causes the moisture content of absorber 3 to decrease. The resulting weight reductions allows pointer 20 to move away from zero and reach equilibrium registering a higher soil moisture potential. Referring to FIG. 2, the equilibrium position is determined primarily by the angular position of calibration weight 22. Weights 22 and 24 are adjustable along screws 23 and 25, respectively to facilitate adjustment of the torques they produce about axis 26 under gravitational force. Adjustable weight 24 functions primarily as a mechanical bias adjustment means. It selects the operating range of the instrument by selecting a clockwise torque about axis 26 produced by weight 24 in combination with absorber 3 which counterbalances the counterclockwise torque produced by arm 20 and weight 22 to achieve equilibrium at a predetermined level of soil moisture potential. Weight 22 has influence on operating range, however, it primarily functions as a mechanical gain adjustment means for adjusting the magnitude of proportional change in moisture potential indication for a given change in the weight of absorber 3. The torque produced by weight 22 varies with the sine of angle 27 formed by the centerline of adjustment screw 23 and the vertical gravitational force vector. Angle 27 is increased as pulley 16 rotates clockwise due to increases in weight of absorber 3 and the counterbalancing torque produced by weight 22 increases proportionately until the assembly reaches equilibrium. The ratio of change in counterbalancing torque to change in angle 27 and thereby the position of pointer 20 is determined by the adjusted position of weight 22 along adjustment screw 23.

The mechanical scale described uses gravitational forces acting on pointer 20 and weights 22 and 24 to counterbalance gravitational force acting on absorber 3. An alternate design could employ springs as a source of counterbalancing force.

Subsurface chamber 6 is constructed of porus material means which is maintained in moisture potential equilibrium with the surrounding soil. Flexible baffle means 70 functions as a vapor barrier which isolates subsurface chamber 6 from the remaining proportions of the instrument. These features minimize affects on instrument accuracy induced by water vapor migration. Water vapor migration having time constants shorter than the time constant for water flow through wick sections 50 and 52 could result from day/night temperature transients. During day to night transitions, the soil temperature decreases at a slower rate than above ground temperatures. Flexible baffle 70 prevents water from evaporating from the warmer absorber and condensing in the cooler above ground portion of the instrument. During night to day transitions, baffle 70 prevents warmer vapors in the above ground portion from condensing on the cooler absorber. The absorber having cooled with the surrounding soil overnight, warms at a slower rate than the above ground portion. On the other hand, the porus material properties of chamber 6 permit relatively free vapor phase migration of moisture between absorption material 5 and the surrounding chamber walls. During day to night transitions, the temperature of absorber 3 will decrease at a slightly slower rate than the soil. The higher temperature of the absorber causes moisture to vaporize from the absorber and condense on the inner surface of chamber 6. The moisture transitions into the wall and on into the surrounding soil as equilibrium is maintained. During night to day transitions, the opposite occurs. Moisture vaporizes from the chamber walls and condenses on the absorber as the surrounding soil increases in temperature at a slightly faster rate than absorber 3. The porus chamber walls permit return of moisture to absorber 3 in the vapor phase to replace that evaporated during day to night transitions to minimize the accumulation of dissolved salts in absorber 3 which could affect calibration accuracy of the instrument.

Figure 4:
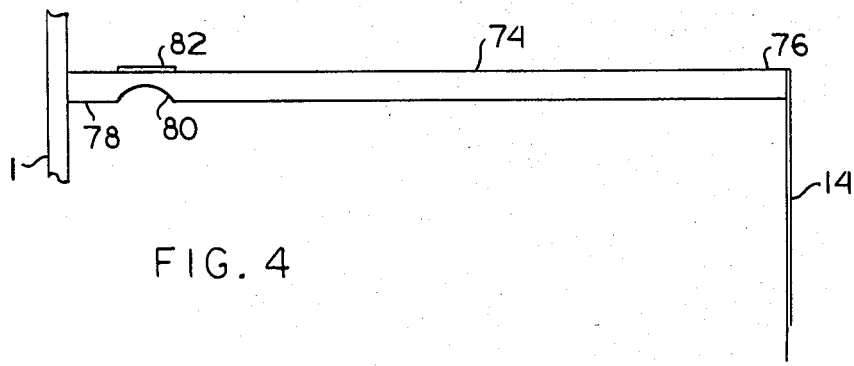
FIG. 4 shows an electro-mechanical transducer for obtaining electrical signals corresponding to the weight of the absorber.
Figure 5:
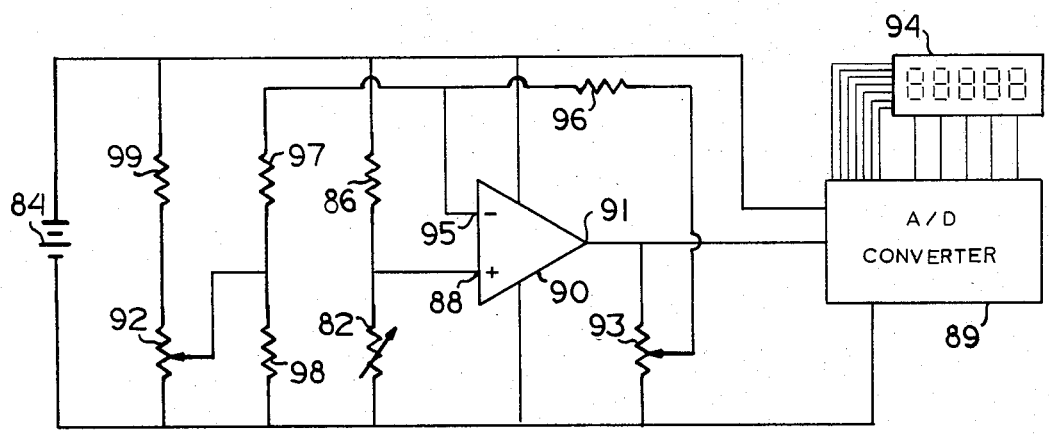
FIG. 5 is a simplified circuit showing employment of the electro-mechanical transducer for making weight measurements of the absorber. The circuit also shows controls for making calibration adjustments.

FIGS. 4 and 5 show an electronic scale means for measuring the weight of absorber 3 as opposed to the mechanical scale means shown in FIGS. 1 and 2. The electronic scale means includes an indicator means comprised of an electro-mechanical transducer means which includes load bar 74 and strain gage 82 shown in FIG. 4, and resistor 86 shown in FIG. 5. Referring to FIG. 5, the indicator means further includes a power source means comprise of battery 84, and a meter means comprised of amplifier 90, analog to digital converter 89 and digital display 94. The electronic scale means further includes a bias calibration means comprised of an electrical bias control means which includes resistor 99 and variable resistor 92, and a gain calibration means comprised of an electrical gain control means which includes variable resistor 93 and resistors 96, 97 and 98.

Referring to FIG. 4, bar 74 has one end fixed to structure 1. Belt 14 is attached to the opposite end so that bar 74 supports the weight of absorber 3. Strain gage 82 is attached to bar 74 at stress concentration notch 80. The weight of absorber 3 produces a bending strain in bar 74 which is enhanced by notch 80 for actuation of gage 82. Bar 74 functions as a spring for counterbalancing gravitational forces acting on said absorber means. Gage 82 is actuated such that its electrical impedance has correspondence with the weight of absorber 3 and thereby the moisture potential of the soil being measured. Strain gage 82 is connected in the electronic circuit shown in FIG. 5. Operating power is provided by battery 84. Resistor 86 and strain gage 82 form a voltage divider so that the voltage supplied to non-inverting input 88 of amplifier 90 varies with the impedance of strain gage 82. The voltage at input 88 is amplified by amplifier 90 and supplied to analog to digital converter 89 where it is converted to a digital signal for readout o display 94. The output of amplifier 90 displayed on digital display 94 has correspondence with the impedance of gage 82 and thereby the moisture potential of the soil being measured. Variable resistor 93 is adjustable to control the magnitude of feedback voltage coupled to inverting input 95 by the voltage divider formed by resistors 96, 97, and 98. Variable resistor 93 controls the gain of amplifier 90 and thereby the proportional change in the magnitude of the number displayed on display 94 for a given change in weight of absorber 3 so that the display can be adjusted to show desired units of soil moisture potential. Variable resistor 92 forms a voltage divider with resistor 99 and applies a voltage across resistor 98 so that a bias voltage is coupled to inverting input 95 by resistor 97. Variable resistor 92 is adjustable to supply a bias voltage to input 95 which counterbalances the voltage supplied to input 88 and causes the output of amplifier 90 to be zero for a preselected weight of absorber 3 in order to select an operating range for the instrument.

What is claimed is:

1. An instrument for measuring soil moisture potential, said instrument being positioned in contact with the soil being measured and comprising:
    a. A structure means joined to an absorber means by a coupling means and a scale means, said structure means providing containment and physical mounting means for said absorber means, said coupling means and said scale means, said structure means including a subsurface chamber means, a baffle means and an above surface section chamber means, said chamber means being installed in direct contact with said soil, said absorber means being mounted internal to said chamber means, said scale means being mounted to said above surface section means, said coupling means being mounted to said chamber means, said absorber means being coupled to said scale means and suspended internal to said chamber means under gravitational force;
    b. Said coupling means movably coupling said absorber means to said soil and facilitating water flow between said absorber means and said soil to effect moisture potential equilibrium of said absorber means with said soil, said absorber means absorbing water and maintaining moisture potential equilibrium with said soil, said scale means weighing said absorber means to determine moisture content thereof and provide an indication of soil moisture potential, said coupling means offering minimum resistance to movement of said absorber means to permit accurate weight measurements thereof;
    c. Said scale means including an indicator means, a bias calibration means and a gain calibration means, said indicator means being an integral part of said scale means and providing a visible indication of soil moisture potential, said bias calibration means being coupled to said indicator means and being adjustable for selecting an operating range for said instrument, said gain calibration means being coupled to said indicator means and being adjustable for selecting ratios of change in soil moisture potential indication to change in weight of said absorber and thereby cause said indicator means to display desired units of soil moisture potential;
    d. Said subsurface chamber means being constructed of porus material means, said baffle means and said porus material means functioning to minimize affects on instrument accuracy due to water vapor migration induced by environmental temperature transients, said baffle means being mounted internal to said structure means and isolating said chamber means to prevent water vapor migration between said absorber means and said above ground section means to minimize affects of water vapor migration on instrument readings, said porus material means being in moisture potential equilibrium with said soil and permitting vapor migration between said material means and said absorber means such that water evaporated from said absorber means can be replaced through water condensation on said absorber during continued termperature cycles to minimize accummulation of dissolved minerals in said absorber which could affect instrument calibration.

2. An instrument for measuring soil moisture potential as disclosed in claim 1 wherein said absorber means comprises a cradle means and a second very fine continuous fiber means, said second fiber means being mounted in said cradle means in a high tension state, said second fiber means functioning when in a high tension state to insure efficient coupling of water flow and moisture potential throughout said absorber means from said coupling means.

3. An instrument for measuring soil moisture potential as disclosed in claim 1 wherein said coupling means comprises a flexible wick means, said wick means extending external to said chamber means for contact with said soil, said wick means functioning to effect efficient coupling of moisture potential of said soil to said absorber means and facilitate water flow bewean said soil and said absorber means to maintain said absorber means in moisture potential equilibrium with said soil, said coupling means offering minimum resistance to motion of said absorber means through flexing of said wick means so as to permit actuation of said scale means by gravitational force acting on said absorber means.

4. An instrument for measuring soil moisture potential as disclosed in claim 2 wherein said wick means comprises a first very fine continuous fiber means and a fiber adjustment means, said fiber adjustment means being mounted in series with said absorber means and said first fiber means and functioning to maintain said first fiber means in a high tension state, said first fiber means functioning when in a high tension state to effect efficient coupling of moisture potential of said soil to said absorber means and facilitate water flow between said soil and said absorber means to maintain said absorber means in moisture potential equilibrium with said soil.

5. An instrument for measuring soil moisture potential as disclosed in claim 4 wherein said first fiber means is configured having two sections mounted in an in-line configuration under tension to form a virtual axis of rotation for said absorber means, said first fiber means offering negledgeable resistance to motion of said absorber means for small rotation angles about said virtual axis, said absorber means being suspended inside said chamber means and coupled to said scale means such that gravitational forces acting on said absorber means cause rotation thereof about said virtual axis, said gravitational forces acting on said absorber means being counterbalanced by said scale means to limit rotation of said absorber means to small angles, said scale means being actuated by gravitational forces acting on said absorber means to provide an indication of weight thereof and thereby of soil moisture potential.

6. An instrument for measuring soil moisture potential as disclosed in any one of the claims 2 and 4 wherein said first and said second very fine continuous fiber means comprises bundles of continuous, very small diameter nylon fibers.

7. An instrument for measuring soil moisture potential as disclosed in any one of the claims 3 and 4 wherein said first fiber means is attached to said second fiber means and said cradle means is configured such that said first fiber means couples tension to said second fiber means to maintain said second fiber means in a high tension state.

8. An instrument for measuring soil moisture potential as disclosed in claim 1 wherein said scale means comprises a mechanical scale means wherein said bias calibration means comprises a mechanical bias adjustment means, said gain calibration means comprises a mechanical gain adjustment means and said indicator means comprises a mechanically actuated pointer means, said pointer means being coupled to said absorber means and configured to change positions in response to changes in weight of said absorber means, changes in position of said pointer means being proportional to changes in gravitational force acting on said absorber means and effecting maintenance of a state of equilibrium wherein said pointer means counterbalances gravitational forces acting on said absorber means, said pointer means providing a visible indication of position thereof and thereby of soil moisture potential, said mechanical bias adjustment means being coupled to said pointer means and adjustable to select a desired equilibrium position for said pointer means for a predetermined soil moisture potential and thereby calibrate said instrument for a desired operating range, said mechanical gain adjustment means being coupled to said pointer means and adjustable to select proportional ratios of magnitude of change in position of said pointer means to magnitude of change in weight of said absorber means to calibrate said instrument to indicate desired units of soil moisture potential.

9. An instrument for measuring soil moisture potential as disclosed in claim 8 wherein said mechanical scale means employs gravitational force to counterbalance gravitational forces acting on said absorber means.

10. An instrument for measuring soil moisture potential as disclosed in claim 8 where said mechanical scale means employs spring force to counterbalance gravitational forces acting on said absorber means.

11. An instrument for measuring soil moisture potential as disclosed in claim 1 wherein said scale means comprises an electronic scale means wherein said bias calibration means comprises an electrical bias control means, said gain calibration means comprises an electrical gain control means and said indicator means comprises a meter means, an electro-mechanical transducer means and a power source means, said power source means being coupled to and supplying operating power to said meter means, said transducer means being mechanically connected to said absorber means and displaying electrical properties having correspondence with weight of said absorber means and thereby with moisture potential of said soil, said meter means being electrically connected to said transducer means and monitoring electrical properties thereof, said meter means visually displaying moisture potential indications having correspondence with electrical properties of said transducer means and thereby with moisture potential of said soil, said bias control means being electrically connected to said meter means and being adjustable to cause said meter means to display a desired moisture potential indication for a predetermined weight of said absorber means and thereby functioning to calibrate said instrument for a desired operating range, said gain control means being adjustable and electrically connected to said meter means to select proportional ratios of magnitude of change in moisture potential indication displayed thereon to magnitude of change in weight of said absorber means to calibrate said instrument to display desired units of soil moisture potential.

12. An instrument for measuring soil moisture potential as disclosed in claim 11 wherein said meter means comprises an amplifier and a digital display.

* * * * *